(12) United States Patent
Schaeffer et al.

(10) Patent No.: US 8,469,989 B2
(45) Date of Patent: Jun. 25, 2013

(54) PUSHABLE COAXIAL BALLOON CATHETER

(75) Inventors: Darin G. Schaeffer, Bloomington, IN (US); David G. Burton, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 231 days.

(21) Appl. No.: 12/968,893

(22) Filed: Dec. 15, 2010

(65) Prior Publication Data
US 2012/0158035 A1    Jun. 21, 2012

(51) Int. Cl.
*A61M 29/00*    (2006.01)

(52) U.S. Cl.
USPC .......... 606/194; 604/96.01; 604/103.04; 604/103.05; 604/103.09; 606/198; 623/1.11

(58) Field of Classification Search
USPC .......... 606/191–199; 604/96.01, 103.04, 604/103.05, 103.09, 525–527; 623/1.11
See application file for complete search history.

(56) References Cited

U.S. PATENT DOCUMENTS

| | | | |
|---|---|---|---|
| 2,930,377 A | 3/1960 | Cowley | 128/344 |
| 3,606,889 A | 9/1971 | Arblaster | 128/349 |
| 4,820,349 A | 4/1989 | Saab | 128/344 |
| 4,896,670 A | 1/1990 | Crittenden | 604/194 |
| 4,917,666 A | 4/1990 | Solar et al. | 604/95 |
| 5,032,113 A | 7/1991 | Burns | 604/96 |
| 5,042,985 A * | 8/1991 | Elliott et al. | 606/192 |
| 5,247,942 A | 9/1993 | Prather et al. | 128/772 |
| 5,318,529 A | 6/1994 | Kontos | 604/96 |
| 5,759,191 A | 6/1998 | Barbere | 606/194 |
| 6,066,157 A | 5/2000 | Barbere | 606/194 |
| 6,706,010 B1 | 3/2004 | Miki et al. | 604/43 |
| 6,808,510 B1 | 10/2004 | DiFiore | 604/171 |
| 7,597,709 B2 * | 10/2009 | Goodin | 623/1.11 |
| 7,708,931 B2 | 5/2010 | Schaeffer et al. | 264/516 |
| 2007/0005092 A1 * | 1/2007 | Godin et al. | 606/194 |
| 2009/0247945 A1 | 10/2009 | Levit et al. | 604/103 |
| 2009/0312831 A1 | 12/2009 | Dorn | 623/1.11 |

FOREIGN PATENT DOCUMENTS

| | | |
|---|---|---|
| EP | 0318918 B1 | 12/1992 |
| EP | 0452901 B1 | 1/1996 |
| JP | 4002363 A | 1/1992 |
| WO | WO 89/08471 A1 | 9/1989 |

* cited by examiner

*Primary Examiner* — Gary Jackson
*Assistant Examiner* — Katrina Stransky
(74) *Attorney, Agent, or Firm* — Brinks Hofer Gilson & Lione (57) ABSTRACT

Coaxial balloon catheters are described herein. The balloon catheter can include outer and inner tubes in a coaxial relationship, with a balloon attached to an end thereof. A support sleeve can be disposed around the inner tubular member proximate the proximal end of the balloon. The support sleeve can have a channel formed therein to communicate with an inflation lumen and a balloon interior. The channel may be formed by separation of two longitudinal edges extending through the support sleeve. The support sleeve can include an outward extending portion that is sized to engage the distal end of the outer tube in order to limit relative movement between the inner and outer tubes. The support sleeve can be configured to orient the inner tube eccentrically or concentrically relative to the outer tube. The support sleeve can have an elongate body that can be extended in proximal or distal direction.

20 Claims, 4 Drawing Sheets

PUSHABLE COAXIAL BALLOON CATHETER

TECHNICAL FIELD

The present disclosure relates to medical devices, and more particularly, to balloon catheters used to dilate narrowed portions of a lumen.

BACKGROUND

Balloon catheters are widely used in the medical profession for various intraluminal procedures. One common procedure involving the use of a balloon catheter relates to angioplasty dilation of coronary or other arteries suffering from stenosis (i.e., a narrowing of the arterial lumen that restricts blood flow).

Although balloon catheters are used in many other procedures as well, coronary angioplasty using a balloon catheter has drawn particular attention from the medical community because of the growing number of people suffering from heart problems associated with stenosis. As a result, there has been an increase in demand for medical procedures to treat such problems. The widespread frequency of heart problems may be due to a number of societal changes, including the tendency of people to exercise less while eating greater quantities of unhealthy foods, in conjunction with the fact that people generally now have longer life spans than previous generations. Angioplasty procedures have become a popular alternative for treating coronary stenosis because angioplasty procedures are considerably less invasive than other alternatives. For example, stenosis of the coronary arteries has traditionally been treated with bypass surgery. In general, bypass surgery involves splitting the chest bone to open the chest cavity and grafting a replacement vessel onto the heart to bypass the blocked, or stenosed, artery. However, coronary bypass surgery is a very invasive procedure that is risky and requires a long recovery time for the patient.

To address the increase in demand for coronary artery treatments, the medical community has turned to angioplasty procedures, in combination with stenting procedures, to avoid the problems associated with traditional bypass surgery. Typically, angioplasty procedures are performed using a balloon-tipped catheter that may or may not have a stent mounted on the balloon (also referred to as a stented catheter). The physician performs the angioplasty procedure by introducing the balloon catheter into a peripheral artery (commonly one of the leg arteries) and threading the catheter to the narrowed part of the coronary artery to be treated. During this stage, the balloon is uninflated and collapsed onto the shaft of the catheter in order to present a low profile which may be passed through the arterial lumens.

Once the balloon is positioned at the narrowed part of the artery, the balloon is expanded by pumping an inflation solution through the catheter to the balloon. As a result, the balloon presses against the inner wall of the artery for dilation thereof. Typical inflated pressures of the balloon may range between about 6 atm to about 20 atm (i.e., 90 psi-300 psi). If a stent is mounted on the balloon, the balloon inflation also serves to expand, as well as implant, the stent within the artery. After the artery is dilated, the balloon is deflated to collapse onto the shaft of the catheter. The balloon-tipped catheter is then retracted from the body. If a stent were mounted on the balloon of the catheter, the stent would be left permanently implanted in an expanded state at the desired location in the artery to provide a support structure that prevents the artery from collapsing back to its pre-dilated condition. On the other hand, when the balloon catheter is not adapted for delivery of a stent, either a balloon-expandable stent or a self-expandable stent may be implanted in the dilated region in a follow-up procedure. Although the treatment of stenosed coronary arteries is one common example where balloon catheters have been used, this is only one example of how balloon catheters may be used and many other uses are also possible.

Conventional angioplasty techniques can be performed with coaxial balloon catheters. A typical coaxial balloon catheter includes an inner tube and an outer tube coaxially disposed about the inner tube. The inner tube defines a lumen for receiving the guidewire. The area between the inner and outer tubes defines an annular lumen for the passage of inflation fluid. For some applications, a coaxial balloon catheter may be advantageous since its delivery profile may be generally smaller than other kinds of balloon catheters, such as a dual-lumen catheter shaft.

One problem that may be encountered with conventional angioplasty techniques with coaxial balloon catheters is the tendency of the balloon portion to become deformed and wrinkled like an accordion when being inserted into a narrowed site of the body lumen. This tendency can be a result of the amount of axial force forced applied by a physician to situate the balloon portion and distal tip of the inner shaft within the narrowed site, which can cause the inner shaft to move proximally relative to the outer shaft. The amount of relative movement between the shafts can be significant enough to compress or buckle the inner shaft to a degree of permanent deformation. Permanent deformation of the inner shaft can make pushability of the coaxial balloon catheter poorer as the axial force applied at the proximal end will not be sufficiently transferred to the distal end. Further, the ends of the balloon portion can be drawn together sufficiently to deform or wrinkle the balloon portion, which expands the delivery profile of the balloon portion greater than its initial folded state. As a consequence, reintroduction of the coaxial balloon catheters through the introducer sheath and a hemostatic valve that is typically included on the sheath, as well as through other narrowed sites, for additional dilations can become more difficult.

BRIEF SUMMARY

Accordingly, a coaxial balloon catheter is provided herein to address at least some of the needs described above. The balloon catheter includes an outer tubular member including a passageway about a longitudinal axis and a distal end. An inner tubular member can be situated within the passageway of the outer tubular member to define an annular lumen, which may be configured to receive an inflation fluid. The inner tubular member can include a lumen and a distal end, where the lumen may be configured to receive a guidewire therethrough. Further included on the balloon catheter is a balloon member that has a proximal end region, a distal end region, and an intermediate working region therebetween. A portion of the proximal end region can be attached to the distal end of the outer tubular member. A portion of the distal end region can be attached to the distal end of the inner tubular member. The balloon member defines a balloon interior in communication with the annular lumen. The balloon member is movable between an inflated state when the balloon interior receives the inflation fluid from the annular lumen and a deflated state when the inflation fluid is removed from the balloon interior. A support sleeve can be disposed around the inner tubular member proximate the proximal end region of the balloon member, and fixed to at least one of the inner and outer tubular members. The support sleeve can have a channel formed therein to communicate with the inflation lumen and the balloon interior. An outward extending portion can be included on the support sleeve. The outward extending portion can be sized to engage the distal end of the outer tubular member in order to limit relative movement between the inner and outer tubular members.

Further, another example of a balloon catheter is provided herein. The balloon catheter can include an outer tubular member and an inner tubular member situated within the passageway of the outer tubular member to define an annular lumen. A balloon member can be included, having a proximal end region, a distal end region, and an intermediate working region therebetween. A portion of the proximal end region can be attached to the outer tubular member, and a portion of the distal end region can be attached to the inner tubular member. The balloon member defines a balloon interior in communication with the annular lumen. The balloon member is movable between an inflated state when the balloon interior receives an inflation fluid from the annular lumen and a deflated state when the inflation fluid is removed from the balloon interior. A support sleeve can have an outward extending portion and an elongated body extending axially from the outward extending portion. The support sleeve can include a wall that defines an axial aperture extending through the outward extending portion and the elongated body. The axial aperture can be configured to receive and attach to the inner tubular member. The wall may have a first longitudinal edge and a second longitudinal edge separated from one another to define a fluid channel. The fluid channel can be in communication with the annular lumen and the balloon interior. The axial aperture can be oriented within the support sleeve so that the inner tubular member is eccentrically offset within the outer tubular member.

Further provided herein is a method of treating a treatment site along a body lumen. The method can include introducing a balloon catheter with a balloon member in a deflated state to a body lumen. The balloon catheter can include an outer tubular member including a passageway, and an inner tubular member including a lumen. The inner tubular member can be situated within the passageway of the outer tubular member to define an annular lumen. The balloon member can have a proximal end region, a distal end region, and an intermediate working region therebetween. A portion of the proximal end region can be attached to the outer tubular member, and a portion of the distal end region can be attached to the inner tubular member. The balloon member defines a balloon interior in communication with the annular lumen. A support sleeve can be disposed around the inner tubular member, and fixed to at least one of the inner and outer tubular members. The support sleeve can have a channel formed therein to communicate with the inflation lumen and the balloon interior, and an outward extending portion sized to engage the proximal end region of the balloon member. The balloon member can be translated to the treatment site. The balloon member can be inflated from the deflated state to an inflated state at the treatment site.

DETAILED DESCRIPTION OF THE DRAWINGS AND THE PRESENTLY PREFERRED EMBODIMENTS

For the purposes of promoting an understanding of the principles of the present disclosure, reference will now be made to the embodiments illustrated in the drawings, and specific language will be used to describe the same.

In the following discussion, the terms "proximal" and "distal" will be used to describe the opposing axial ends of various component features. The term "proximal" is used in its conventional sense to refer to the end of the apparatus (or component thereof) that is closest to the operator during use of the apparatus. The term "distal" is used in its conventional sense to refer to the end of the apparatus (or component thereof) that is initially inserted into the patient, or that is closest to the patient during use.

Figures 1A, 1B:
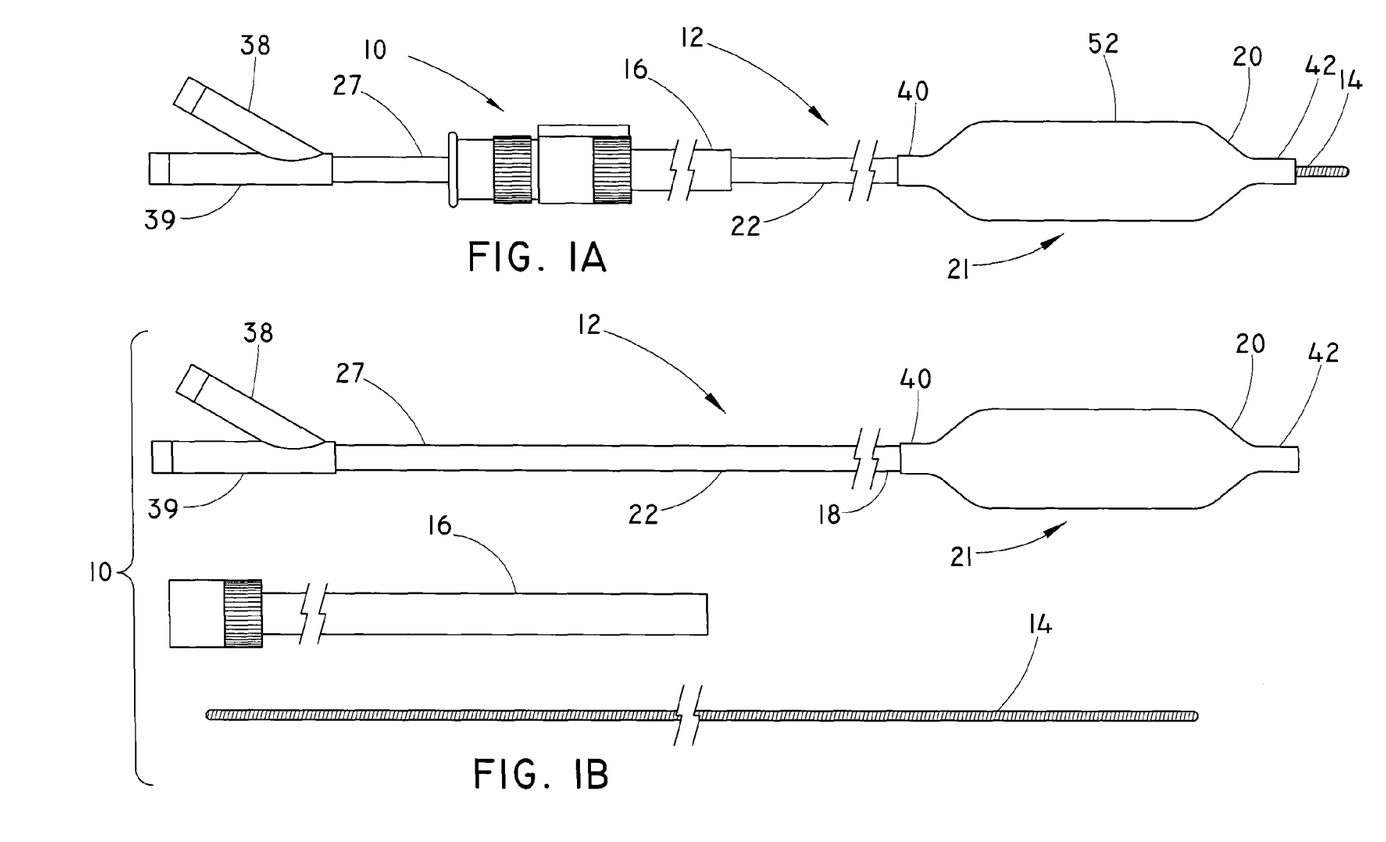
FIG. 1A is a side view of a catherization kit for use in a body lumen, including a balloon catheter.
FIG. 1B is an exploded side view of the catherization kit in FIG. 1A, with the balloon catheter in an inflated state.

FIGS. 1A-1B show a kit 10 for balloon catherization of a body lumen, such as a body vessel, sinus region, airway, tracheostomies, etc. Kit 10 can include a balloon catheter 12, a guidewire 14, and an introducer sheath 16.

Figure 2:
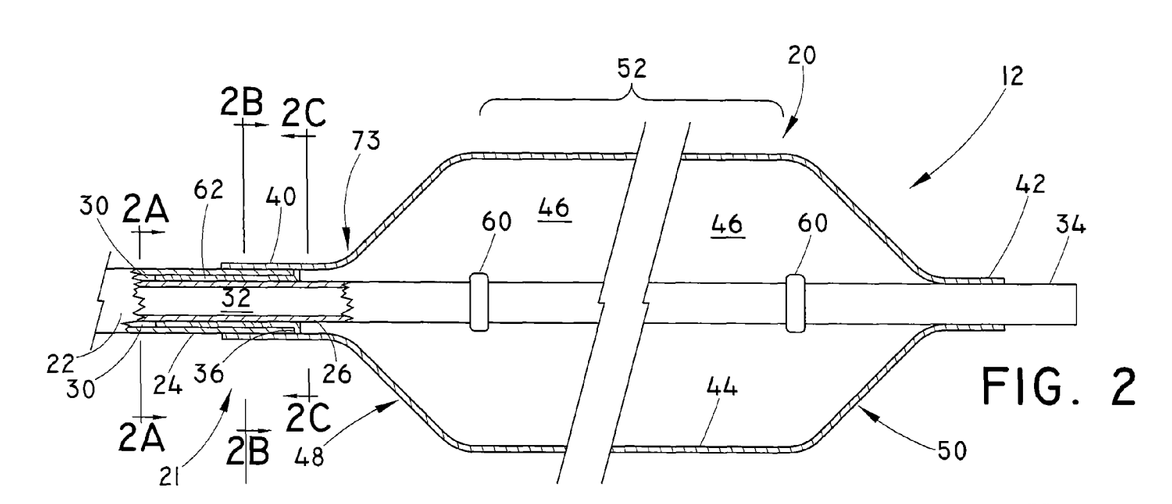
FIG. 2 is a partial sectional view of a distal portion of a balloon catheter, depicting a support sleeve.
Figure 2A:
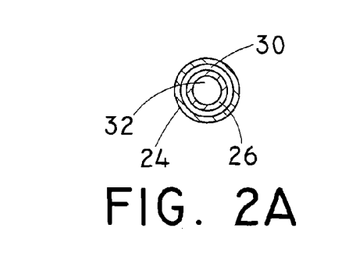
FIGS. 2A-2C are transverse cross-sectional views taken along lines 2A-2A, 2B-2B, and 2C-2C, respectively, of the balloon catheter of FIG. 2.

With additional reference to FIG. 2, balloon catheter 12 comprises a balloon 20 disposed at a distal portion 21 of a shaft 22. Shaft 22 comprises an outer tubular member 24 and an inner tubular member 26. Outer and inner tubular members 24, 26 can be structured and arranged in a coaxial relationship such that an annular lumen is formed therebetween, thereby forming an inflation lumen 30, which is also shown in FIG. 2A. Inner tubular member 26 can have a lumen 32 formed therein, which can span from a proximal end to a distal end 34 of inner tubular member 26. Lumen 32 is configured to receive guidewire 14 and/or other medical components. For instance, guidewire 14 may be delivered percutaneously to a site of a vascular condition, and balloon catheter 12 may be delivered over guidewire 14 by placing distal end 34 of inner tubular member 26 over an end of the guidewire and advancing balloon catheter 12 distally over the guidewire while balloon 20 is in a deflated state.

Inner tubular member 26 can extend distally beyond a distal end 36 of outer tubular member 24. To this end, balloon 20 can be attached between outer and inner tubular members 24, 26 in order to be in fluid communication with inflation lumen 30. For example, balloon 20 includes a proximal attachment region 40 and a distal attachment region 42. Proximal attachment region 40 can be attached to surround an exterior surface of outer tubular member 24 proximate distal end 36 thereof, while distal attachment region 42 is attached to surround an exterior surface of inner tubular member 26 proximate distal end 34 thereof.

Balloon 20 is a tubular structure having a balloon wall 44 defining a balloon lumen 46 that is between an interior surface of balloon wall 44 and the exterior surface of inner tubular member 26. Balloon lumen 46 is in fluid communication with inflation lumen 30. Accordingly, distal end 36 of outer tubular member 24 can terminate proximate proximal attachment region 40 of balloon 20, such that inflation fluid delivered via inflation lumen 30 is channeled to balloon lumen 46 to achieve inflation of balloon 20 to an inflated state. As shown, inner tubular member 26 may extend at least to the distal attachment region 42 of balloon 20, if not beyond, so that lumen 32 is not in fluid communication with balloon lumen 46.

Balloon 20 may comprise any number of configurations. For example, balloon 20 can include a proximal taper or cone 48, a distal taper or cone 50, and an intermediate working region 52 formed therebetween. Proximal and distal attachment regions 40 and 42 of balloon 20 can be tubular shaped members extending from the respective tapers 48, 50. Working region 52 may be sized and configured to dilate the body lumen, such as to perform angioplasty on a luminal wall of a body vessel. Alternatively, balloon 20 may have proximal and distal regions and comprise other shapes, such as circular, oval, dogbone, conical or tapered or the like known by one of ordinary skill in the art.

Referring back to FIGS. 1A-1B, shaft 22 can further include an injection port 38 at a proximal end 27 thereof. Injection port 38 can provide access for injecting a fluid to be advanced through inflation lumen 30 for inflation of balloon 20 to an inflated state (shown in FIG. 2). The fluid may also be removed from balloon 20 through inflation lumen 30 and injection port 38 to collapse balloon 20 to a deflated state, as can be appreciated by those skilled in the art. In one example, balloon 20 in the inflated state can have an internal pressure of at least about 5 atmospheres, and balloon 20 in the deflated state can have a pressure of less than about 5 atmospheres and preferably between about 0 and 1 atmosphere (0.0 to 14.7 psi or −14.7 to 0.0 psig).

In addition, introducer sheath 16 can be used to percutaneously introduce guidewire 14 and balloon catheter 12 into a body lumen. Introducer sheath 16 can be made of polytetrafluoroethylene (PTFE) or any other suitable material for intravascular use. The introducer sheath may be any suitable size, such as, for example, between about 3 French to 8 French. Introducer sheath 16 can receive and provide stability to balloon catheter 12 at a desired location of the body lumen. For example, as introducer sheath 16 is held stationary within the body lumen, the introducer sheath adds stability to balloon catheter 12 while being advanced through the introducer sheath to the desired treatment location in the body lumen.

Moreover, guidewire 14 can be configured to be percutaneously inserted within the body lumen to guide balloon catheter 12 to the desired location. Guidewire 14 may be manipulated through a wire guide port 39 of balloon catheter 12. Lumen 32 of balloon catheter 12 is fed over the proximal end of guidewire 14 to provide balloon catheter 12 with a path to follow when advanced within the body lumen. The guidewire may be of different weights and flexibilities depending on the application. The guidewire may have soft, flexible tips, which may be shorter or longer, as well as straight or bowed. A central lumen may be provided in the guidewire for pressure measurements and injections of contrast medium. When balloon 20 is at the desired location in the body lumen, guidewire 14 may optionally be removed. Balloon 20 may then be inflated to the inflated state for treating the body lumen. After treatment of the body lumen, balloon 20 can be retracted by collapsing the balloon 20 into the deflated state and retracting balloon 20 into a lumen of introducer sheath 16 for retrieval of balloon catheter 12 from the body lumen.

According to FIG. 2, balloon catheter 12 may include one or more radiopaque markers 60 disposed near the distal portion 21 of shaft 22. For example, the shaft 22 can include two radiopaque markers 60 disposed annularly around the outside of inner tubular member 26 within balloon 20 adjacent to each end of balloon 20. The markers 60 can be used to fluoroscopically determine the position of balloon 20 within the body lumen of the patient. Suitable markers 60 may comprise gold or other high-density materials that are viewable with a fluoroscope.

A support sleeve can be located to surround the inner tubular member proximate the proximal attachment region of the balloon. The support sleeve can be attached to the inner tubular member and/or the outer tubular member. The support sleeve is configured to reduce the tendency of relative axial movement between the outer and inner tubular members, thereby reducing the risk of deformation or wrinkling of the balloon.

Figure 3:
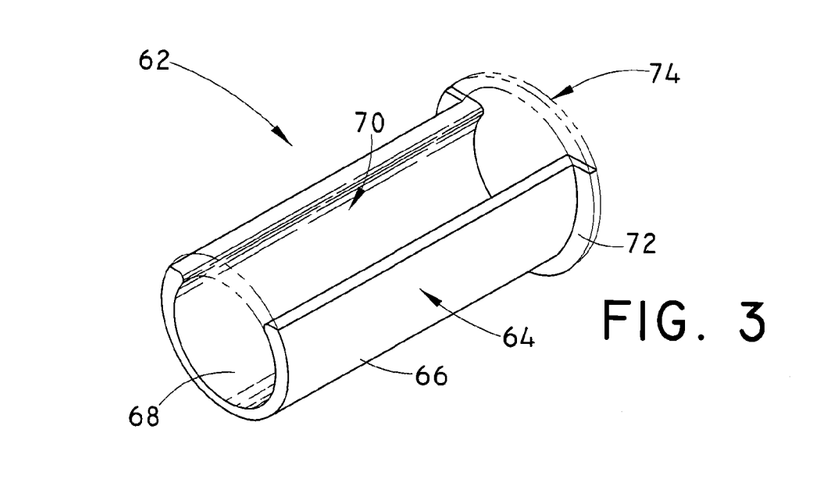
FIG. 3 is a perspective view of a support sleeve.

FIG. 3 depicts one embodiment of the support sleeve, referred to as reference numeral 62, which is shown situated in place in FIG. 2. Support sleeve 62 can be a tubular elongated structure having a wall 64 extending longitudinally with an outer surface 66 and an inner surface 68. Wall 64 can have a first removed portion, shown generally in dashed lines, for forming longitudinal edges that define a channel 70 generally between the confronting surfaces of the outer and inner tubular members. Channel 70 is configured to permit inflation lumen 30 to communicate with balloon lumen 46 when the support sleeve is disposed along the inner tubular member. Channel 70 can extend longitudinally as shown in the figure.

Support sleeve 62 may further include a radial lip 72 extending outward beyond the general outer surface 66. Radial lip 72 may be formed to surround wall 64 completely. Optionally, radial lip 72 may be formed with a second removed portion, shown generally in dashed lines, for forming circumferential edges that define another portion 74 of channel 70 generally between the confronting surfaces of the inner tubular member and the proximal attachment region of the balloon. Channel 70 and portion 74 can be formed with a chordal cut (FIG. 4A) to form portion 74A, a wedged cut (FIG. 4B) to form portion 74B, or in any other manner known in the art.

Figure 2B:
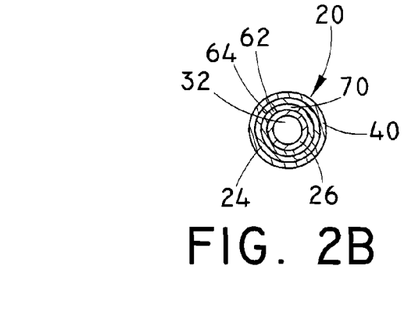

As shown in FIG. 2, support sleeve 62 can be oriented such that a substantial portion of wall 64 is disposed within inflation lumen 30 formed by the annular lumen between tubular members 24, 26 and radial lip 72 is located just beyond distal end 36 of outer tubular member 24. Support sleeve 62 can be attached or bonded to outer tubular member 24, the inner tubular member 26, or both, with the attachment means described hereinbelow, and is preferably attached to inner tubular member 26. As shown in FIG. 2B, the elongated wall 64 has a transverse cross-section sized to substantially fill the annular lumen between the outer and inner tubular members 24, 26, except for channel 70. In this configuration, outer surface 66 can have an outer diameter that is approximately identical to the luminal diameter of outer tubular member 24. Further, inner surface 68 can have an inner diameter approximately identical to the outer diameter of inner tubular member 26. To this end, support sleeve 62 can reinforce the attachment between the tubular members 24, 26 in order to inhibit relative movement therebetween. Radial lip 72 can also provide a physical stop in the axial path of outer tubular member 24 to further inhibit relative movement between the tubular members. The distal end edge of outer inner tubular member 24 can contact the adjacent, confronting surface of radial lip 72, and may be further attached or bonded thereto with the attachment means described hereinbelow. Alternatively, the confronting surface may be spaced from the distal end edge of the outer tubular member to limit relative movement between the tubular members to a greater predefined distance. The spacing can be, e.g., about 1 mm to about 15 mm.

Figure 2C:
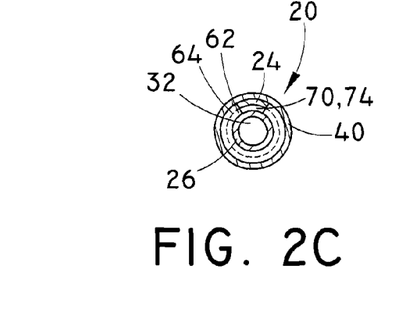

The outermost radial extent of radial lip 72 can be approximately equal to the outer diameter of outer tubular member 24. Radial lip 72 can also provide a support in the radial direction to maintain proximal attachment region 40 of balloon 20 in the desired profile, and to further prevent radial compression of inner tubular member 26, as shown in FIG. 2C. Radial lip 72 may also be configured to extend along and engage the luminal wall of outer tubular member 24, i.e., the outer tubular member can extend over the radial lip. Moreover, with reference to FIG. 2, support sleeve 62 can be situated proximate the intersection 73 of proximal taper 48 and proximal attachment region 40 of balloon 20. Preferably, support sleeve 62 is positioned outside balloon lumen 46, proximal to intersection 73, so that preferably no portion of the support sleeve protrudes into balloon lumen 46. By this arrangement, possible obstructions are removed from within balloon lumen 46 so that balloon 20 can be more easily re-folded to a delivery profile for reintroduction into the introducer sheath and other narrowed portions of the body lumen.

In some instances, it may be desirable to attach support sleeve 62 to only one of outer tubular member 24 or inner tubular member 26, but not both. This arrangement can permit some limited relative movement between the outer and inner tubular members. For example, during inflation of the balloon the inner tubular member may be urged to move distally relative to the outer tubular member. Some limited relative movement can also be desirable to permit the balloon to elongate during deflation and assume a minimal cross-section in order to be withdrawn through the introducer sheath and out of the body. Furthermore, after deflation of the balloon and during reintroduction of the balloon catheter through the introducer sheath, as well as the hemostatic valve, the inner tubular member may be urged to move proximally relative to the outer tubular member. While some proximal movement of the inner tubular member is acceptable, the support sleeve can be positioned along the inner tubular member to provide a physical stop of relative movement until the support sleeve engages the distal end of the outer tubular member.

Figure 3A:
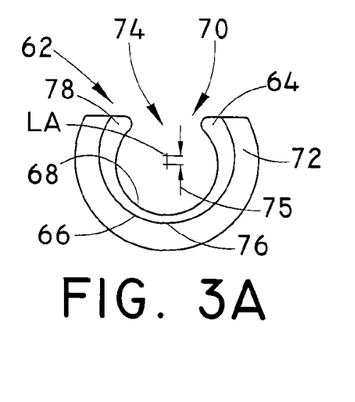
FIG. 3A is an end view of the support sleeve of FIG. 3.
Figure 3B:
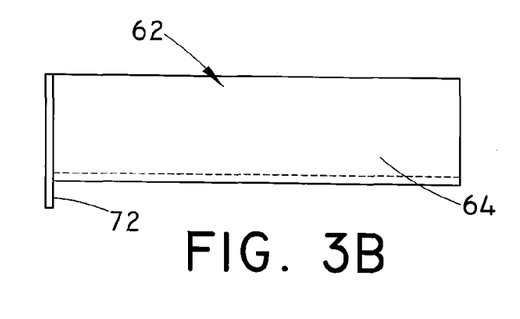
FIG. 3B is a side view of the support sleeve of FIG. 3.
Figure 4A:
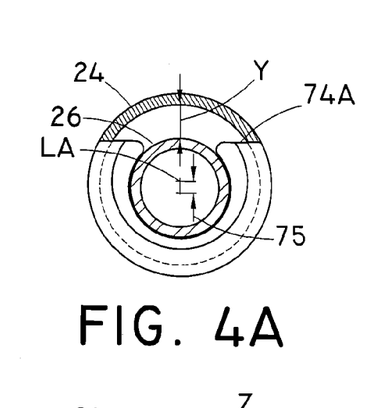
FIG. 4A is an end view of a support sleeve orienting the inner tubular member in an eccentric relationship relative to the outer tubular member.
Figure 4B:
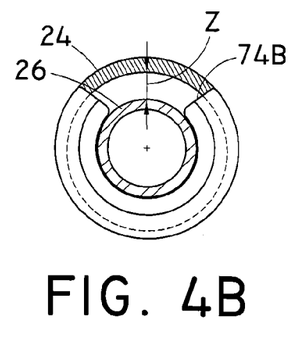
FIG. 4B is an end view of a support sleeve orienting the inner tubular member in a concentric relationship relative to the outer tubular member.

Support sleeve 62 can be configured to centrally locate inner tubular member 26 with respect to the longitudinal axis LA of outer tubular member 24 so that the tubular members are concentric. However, to increase the size of the transverse cross-sectional area of channel 70 and portion 74, support sleeve 62 can be configured to offset inner tubular member 26 with respect to the longitudinal axis LA of outer tubular member 24 so that the tubular members are eccentric, as shown by the spacing 75 in FIGS. 3A and 4A. Increasing the size of the channel can allow an increase in flow rate of the inflation fluid and/or a decrease in inflation fluid pressure. Wall 64 can have a varied transverse cross-sectional thickness with a thin region 76 formed diametrically opposite channel 70 and portion 74. Portions of wall 64 that are contiguous to channel 70 and portion 74 can include a thicker region 78 having a greater wall thickness than thin region 76. The aperture defined by inner surface 68 of support sleeve 62, which has thin region 76 and thicker region 68, is preferably sized to have a general diameter about the same as the outer diameter of inner tubular member 26. The eccentric configuration can increase the size of the inflation fluid path, thereby reducing the fluid pressure used to deliver the inflation fluid and/or increasing the flow rate of the inflation fluid. In FIG. 4B, the arrangement between the inner and outer tubular members is shown as concentric, having a radial spacing Z of channel 70 between the inner surface of outer tubular 24 member and the outer surface of inner tubular member 26. Channel 70 can be increased to radial distance Y as shown in FIG. 4A with an eccentric arrangement, which is the sum of radial distance Z and spacing 75.

Figure 5:
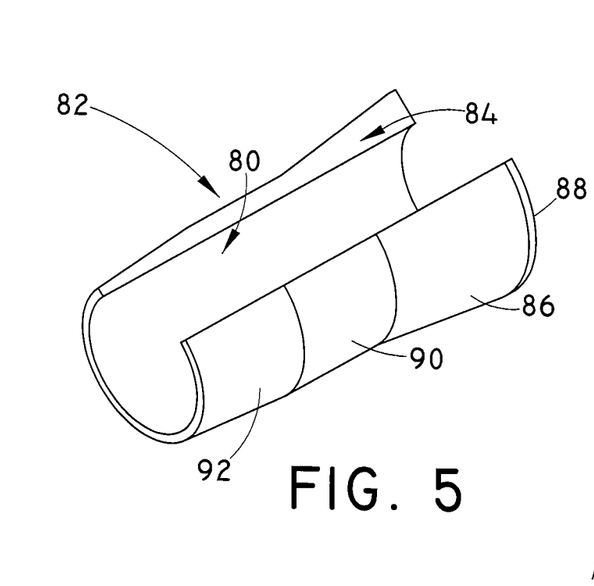
FIG. 5 is a perspective view of another support sleeve.

FIG. 5 depicts another embodiment of the support sleeve, referred to as reference numeral 82. Support sleeve 82 can include at least some, if not all, of the features of support sleeve 62. For example, the wall 84 of support sleeve 82 has a tapered portion 86 leading to an end 88 of the support sleeve. In particular, instead of the sharp transition that is between wall 64 and radial lip 72 shown in FIG. 3, tapered portion 86 can provide as smooth transition to support end 88 thereof. Tapered portion 86 may be gradually extended radially outward to generally have same degree of radial extent as radial lip 72. Support sleeve 82 can also have an intermediate portion 90 that has a uniform thickness, which is situated between tapered portion 86 and an end portion 92 that is shown to be tapered opposite the tapered portion 86.

Figure 6:
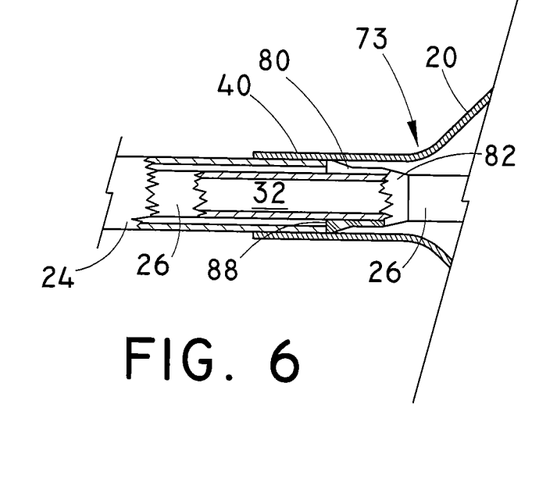
FIG. 6 is a partial sectional view of a distal portion of a balloon catheter, depicting the support sleeve of FIG. 5 in relation to the outer and inner tubular members.

As shown in FIG. 6, support sleeve 82 can be attached to inner tubular member 26. Support sleeve 82 can be oriented such that wall 84 is disposed outside outer tubular member 24, and end 88 is contacted with or attached to distal end 36 of outer tubular member 24. Support sleeve 82 can inhibit relative movement between the tubular members by providing a physical stop in the axial path of outer tubular member 24. Preferably, support sleeve 82 is positioned outside balloon lumen 46, proximal to intersection 73, and does not protrude into balloon lumen 46. As can be appreciated by those skilled in the art, support sleeve 82 can be oriented like support sleeve 62 is shown in the figures, and, vice versa, support sleeve 62 can be oriented like support sleeve 82 is shown. Further, support sleeve 82 can be configured to orient inner tubular member 26 concentric or eccentric relative to outer tubular member 24 as described herein.

Those skilled in the art recognize that there are many ways in which a balloon catheter may be introduced into a body lumen, such as a body vessel, sinus region, airway, tracheostomies, etc., and accordingly, balloon catheter 12 may be introduced in any of these well known ways. The balloon catheter can be introduced to any number of lumens or passages, such as, for example, from a right groin of a patient throughout the length of an artery to an aorta and to coronary arteries, into the sinus passage, or airway. The balloon catheter may be used for a number of tasks, such as, for example, for delivering a stent to a constriction or stenosis in a body vessel, for dilating coronary vessels, for breaking bone in the sinus area, for opening a stenosed airway, and for creating a stoma in an airway, just to name a few examples. The balloon catheter may be any type of balloon catheter which employs the use of a balloon, such as, but not limited to, over-the-wire systems, single-operator exchange systems, fixed wire systems, and perfusion balloons.

For angioplasty, e.g., balloon catheter 12 can be introduced over guidewire 14 that has previously been inserted into a body lumen using, e.g., the well-known Seldinger percutaneous entry technique. Introducer sheath 16 may be introduced over guidewire 14 to provide a conduit for safe passage of balloon catheter 12 to a treatment site, such as a constriction or stenosis in the body vessel. The guidewire may be conveniently rotated and controlled during translation of the distal tip of the guidewire to the distal side of the treatment site in the body lumen. For anatomical orientation, additional doses of contrast medium may be supplied. At this point, the balloon catheter is thrust onto the guidewire external to patient and advanced through the introducer sheath along a track formed by the guidewire into the body lumen and to the stenosis. Depending on the degree of narrowness of the stenosis, when pushing through the stenosis the inner tubular member may move proximally relative to the outer tubular member until the support sleeve engages the outer tubular member. Proper position of the balloon may be verified under a suitable imaging technique, such as x-ray fluoroscopy when the balloon catheter comprises the radiopaque markers, or direct visualization using a scope in the case of sinus or airway applications. Following verification of proper placement, the balloon may be inflated by well-known means. Inflation of the balloon can cause the balloon to engage and thereby dilate the stenosis for treatment with the balloon. During initial inflation, the inner tubular member can more away distally relative to the outer tubular member, and at full inflation the distal ends of the inner and outer tubular members may be brought closer together. The balloon may be deflated and re-inflated one or more additional times if desired. After sufficient treatment of the instant treatment site with the balloon, the balloon can be deflated and the balloon catheter can then be retracted over the guidewire into the introducer sheath. The inner and outer tubular members may move slightly relative to one another during deflation in order to elongate the balloon so that the balloon can assume a minimal profile when being withdrawn through the introducer sheath. The balloon catheter can then removed from the body lumen.

To reintroduce the balloon catheter to another treatment site within the body lumen, the balloon can be refolded and wrapped into the delivery profile. When the balloon catheter is reintroduced, the support sleeve can facilitate retraction of the balloon within the introducer sheath and reintroduction of the balloon over the guidewire to the same treatment site or different treatment sites. In particular, during reintroduction of the balloon catheter through the introducer sheath, and in particular through a hemostatic valve of the introducer sheath, the support sleeve can limit the degree of relative movement between the tubular members. As can be appreciated from the present disclosure, the support sleeve can substantially inhibit the relative movement between the outer and inner tubular members that can be sufficient to cause deformation of the inner tubular member. This arrangement can improve the pushability of the coaxial balloon catheter by permitting sufficient transfer of axial force applied at the proximal end to the distal end during reintroduction of the balloon catheter. Further, the ends of the balloon can be substantially inhibited from being drawn together so that deformation or wrinkling of the balloon is avoided, thereby permitting the balloon to refolded to profile approximating its initial folded stated. Further, the support sleeve can strengthen the joint between the outer and inner tubular members so that radial compression or buckling or axial compression of the inner tubular member is substantially prevented.

With respect to manufacturing and/or assembling the balloon catheter, the inner and outer tubular members can be formed by any methods know in the art, such as by an extrusion process or a multilayer heat shrinking process. The outer and inner tubular members may be made of any appropriate biocompatible material for intravascular use. The outer and inner tubular members may be formed from one or more semi-rigid polymers. For example, the tubular members may be manufactured from polyurethane, polyethylene, polytetrafluoroethylene, fluorinated ethylene propylene, polyamides, tetrafluoroethylene, latex, rubber, and mixtures thereof. A building mandril can be inserted within the inner tubular member, and the radiopaque markers can be attached to the inner tubular member by any means known in the art.

The inner tubular member can be inserted within the support sleeve and the support sleeve can be placed a predetermined distance from the markers for attachment to the inner tubular member. The support sleeve can be micro-machined or micro-molded from any biocompatible thermoset or thermoplastic materials, or stamped from a biocompatible metal such as stainless steel or nitinol. The support sleeve can be then attached to the inner tubular member using an adhesive, such a biocompatible glue, or alternatively, using a heat-bond, heat-shrink tubing, one or more tie-down bands, solvent bonding, ultrasonic welding or the like. A spacer mandril can be inserted into the channel during processing to prevent the channel from being filled up or collapsing during processing. The spacer mandril can be removed after processing to leave the channel open for operation. The inner tubular member can be then inserted through the outer tubular member from the proximal end until the distal end contacts a portion of the support sleeve, such as, e.g., the radial lip of the support sleeve. Depending on medical requirements, the inner and outer tubular members are sized and arranged for the desired inflation lumen size. The support sleeve may also or may not be attached to the outer tubular member. It is contemplated that the support sleeve can be integrally formed with the inner and/or outer tubular members such as by molding techniques.

A balloon material can be attached to the inner and outer tubular members. To accommodate different applications and pressures, the balloon can have various lengths, widths, and wall thicknesses to accommodate various pressures. The balloon may be manufactured from any suitable balloon material used during an interventional procedure, such as an angioplasty procedure. For example, the balloon can be made from a low or non-compliant material, such as, for example, nylon or polyester. The compliant characteristics of the balloon can affect how the physician may use the balloon catheter. A low or non-compliant balloon will increase in diameter by up to a maximum of about 5% of its nominal diameter in response to increasing the inflation pressure to about 5 to about 20 atmospheres. One example use for the low or non-compliant balloon may be for cracking lesions within a restricted portion of the body lumen while minimizing the likelihood of damaging an adjacent non-restricted portion of the body lumen. Alternatively, the balloon may be made from a hybrid or highly compliant material where the diameter of the balloon may increase as much as about 40% during inflation. The hybrid or highly compliant balloon may proportionally increase in diameter in response to increases in inflation pressure, which may allow for fewer balloon sizes to be used to treat a wider range of lumen diameters.

Means of attaching the balloon material, in particular the proximal and distal attachment regions of the balloon, to the respective tubular members, include, for example, heat sealing, using an adhesive, forced convection heating, radio frequency heating, ultrasonic welding, laser bonding, or the like. Shrink tubing may be used as a manufacturing aid to compress and fuse the balloon to the tubular members. The shrink tubing may be removed and disposed of after the balloon is sealed, or may remain on as part of the connected structure. During the attachment process, the proximal attachment region may be attached to a portion of the support sleeve, such as, e.g., the outer surface of the radial lip. Furthermore, the support sleeve may be attached to the both of the inner and outer tubular members after the balloon attachment process. The spacer mandril can be removed prior to attachment of the distal attachment region of the balloon. After suitable attachment, the building mandril can then be removed from the inner tubular member, thereby resulting in a balloon catheter of the present disclosure.

Drawings in the figures illustrating various embodiments are not necessarily to scale. Some drawings may have certain details magnified for emphasis, and any different numbers or proportions of parts should not be read as limiting, unless so-designated in the present disclosure. Those skilled in the art will appreciate that embodiments not expressly illustrated herein may be practiced within the scope of the present invention, including those features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention

We claim:

1. A coaxial balloon catheter comprising:
   an outer tubular member including a passageway about a longitudinal axis and a distal end;
   an inner tubular member including a lumen and a distal end, the inner tubular member situated within the passageway of the outer tubular member to define an annular lumen, the annular lumen configured to receive an inflation fluid;
   a balloon member having a proximal end region, a distal end region, and an intermediate working region therebetween, the proximal end region attached to the outer tubular member, the distal end region attached to the inner tubular member, the balloon member defining a balloon interior in communication with the annular lumen, where the balloon member is movable between an inflated state when the balloon interior receives the inflation fluid from the annular lumen and a deflated state when the inflation fluid is removed from the balloon interior; and
   a support sleeve comprising a wall disposed around a portion of the inner tubular member proximate the proximal end region of the balloon member, the support sleeve being fixed to the inner tubular member while being unattached to the outer tubular member, the inner and outer tubular members thereby being movable relative to each other, the wall of the support sleeve having a removed portion defining a channel formed therein between longitudinal edges of the wall and confronting surfaces of the outer and inner tubular members, the channel communicating with the annular lumen and the balloon interior, and an outward extending portion sized to engage the distal end of the outer tubular member in order to limit relative movement between the inner and outer tubular members.

2. The balloon catheter of claim 1, where the support sleeve further comprises an elongated body extending axially from the outward extending portion, having an aperture extending axially therethrough, the aperture configured to receive the inner tubular member.

3. The balloon catheter of claim 2, where the aperture is oriented within the support sleeve so that the inner tubular member is concentric with the outer tubular member.

4. The balloon catheter of claim 2, where the aperture is oriented within the support sleeve so that the inner tubular member is eccentric with the outer tubular member.

5. The balloon catheter of claim 4, where the wall of the support sleeve has a varying thickness, where a first portion of the wall opposite the channel has a first thickness, and a second portion of the wall adjacent the channel has a second thickness greater than the first thickness, so that the inner tubular member is eccentrically oriented away from the channel.

6. The balloon catheter of claim 2, where the elongated body extends proximally from the outward extending portion into the annular lumen between the tubular members.

7. The balloon catheter of claim 6, where the elongated body has a transverse cross-section sized to substantially fill the annular lumen between the tubular members except for the channel.

8. The balloon catheter of claim 2, where the elongated body extends distally from the outward extending portion away from the annular lumen between the tubular members.

9. The balloon catheter of claim 8, where the elongated body has a tapered portion extending to the outward extending portion.

10. The balloon catheter of claim 1, where the outward extending portion has a confronting surface configured to contact the distal end of the outer tubular member, thereby at least substantially blocking relative movement between the inner tubular member and the outer tubular member.

11. The balloon catheter of claim 1, where the support sleeve is oriented along the inner tubular member so that support sleeve remains substantially external to the balloon interior.

12. A coaxial balloon catheter comprising:
    an outer tubular member including a passageway about a longitudinal axis, and an inner tubular member including a lumen, the inner tubular member situated within the passageway of the outer tubular member to define an annular lumen;
    a balloon member having a proximal end region, a distal end region, and an intermediate working region therebetween, a portion of the proximal end region attached to the outer tubular member, a portion of the distal end region attached to the inner tubular member, the balloon member defining a balloon interior in communication with the annular lumen, where the balloon member is movable between an inflated state when the balloon interior receives an inflation fluid from the annular lumen and a deflated state when the inflation fluid is removed from the balloon interior; and
    a support sleeve having an outward extending portion and an elongated body extending axially from the outward extending portion, a wall defining an axial aperture extending through the outward extending portion and the elongated body, the support sleeve attached to the inner tubular member that is received by the axial aperture, the support sleeve extending through the outer tubular member and being unattached to the outer tubular member, the inner and outer tubular members thereby being moveable relative to each other, the wall having a first longitudinal edge and a second longitudinal edge separated from one another to define a fluid channel in communication with the annular lumen and the balloon interior, where the axial aperture is oriented to eccentrically offset the inner tubular member relative to the outer tubular member.

13. The balloon catheter of claim 12, where the inner tubular member is eccentrically offset away from the location of the fluid channel.

14. The balloon catheter of claim 12, where a first portion of the wall opposite the channel has a first thickness, and a second portion of the wall adjacent the channel along the first and second longitudinal edges has a second thickness greater than the first thickness.

15. The balloon catheter of claim 12, where the elongated body extends proximally from the outward extending portion into the annular lumen between the tubular members.

16. The balloon catheter of claim 12, where the elongated body extends distally from the outward extending portion away from the annular lumen between the tubular members.

17. The balloon catheter of claim 12, where the outward extending portion has a confronting surface configured to contact the distal end of the outer tubular member, thereby at least substantially blocking the inner tubular member from proximally moving relative to the outer tubular member.

18. The balloon catheter of claim 12, where the support sleeve is oriented along the inner tubular member so that support sleeve remains substantially external to the balloon interior.

19. A method of treating a treatment site along a body lumen, comprising:

introducing a balloon catheter with a balloon member in a deflated state into a body lumen, where the balloon catheter includes an outer tubular member including a passageway, an inner tubular member including a lumen, the inner tubular member situated within the passageway of the outer tubular member to define an annular lumen, the balloon member having a proximal end region, a distal end region, and an intermediate working region therebetween, a portion of the proximal end region attached to the outer tubular member, a portion of the distal end region attached to the inner tubular member, the balloon member defining a balloon interior in communication with the annular lumen, and a support sleeve comprising a wall defining an axial aperture extending therethrough disposed around a portion of the inner tubular member, the support sleeve being fixed to at least one of the inner and outer tubular members while being unattached to the other of the inner and outer tubular members, the inner and outer tubular members thereby being movable relative to each other, the wall of the support sleeve having a removed portion defining a channel formed therein between longitudinal edges of the wall and confronting surfaces of the outer and inner tubular members, the channel communicating with the inflation lumen and the balloon interior, where the axial aperture is oriented to eccentrically offset the inner tubular member relative to the outer tubular member away from the channel, and an outward extending portion sized to engage the proximal end region of the balloon member;

translating the balloon member to the treatment site; and inflating the balloon member from the deflated state to an inflated state at the treatment site.

20. The method of claim 19, where the support sleeve is further configured to eccentrically offset the inner tubular member relative to the outer tubular member.

\* \* \* \* \*